United States Patent [19]

Dershem et al.

[11] Patent Number: 5,753,748
[45] Date of Patent: May 19, 1998

[54] BLEED RESISTANT CYANATE ESTER-CONTAINING COMPOSITIONS

[75] Inventors: Stephen M. Dershem; Deborah L. Derfelt, both of San Diego, Calif.

[73] Assignee: Quantum Materials, Inc., San Diego, Calif.

[21] Appl. No.: 687,363

[22] PCT Filed: Apr. 11, 1996

[86] PCT No.: PCT/US96/04960

§ 371 Date: Aug. 2, 1996

§ 102(e) Date: Aug. 2, 1996

[87] PCT Pub. No.: WO96/35760

PCT Pub. Date: Nov. 14, 1996

Related U.S. Application Data

[63] Continuation of Ser. No. 479,006, Jun. 7, 1995, Pat. No. 5,646,241, which is a continuation-in-part of Ser. No. 439,975, May 12, 1995, abandoned.

[51] Int. Cl.$^6$ .................... C08K 5/17; C08K 5/49; H01B 1/20
[52] U.S. Cl. .................... 524/714; 524/440; 524/709; 524/236; 528/422; 252/500; 252/511
[58] Field of Search .................... 524/709, 714; 528/422; 252/500, 511

[56] References Cited

U.S. PATENT DOCUMENTS

| | | | |
|---|---|---|---|
| 4,401,776 | 8/1983 | Munk | 523/443 |
| 4,483,898 | 11/1984 | Schonhorn et al. | 428/356 |
| 4,513,114 | 4/1985 | Kunugi et al. | 524/709 |
| 4,552,690 | 11/1985 | Ikeguchi et al. | 252/512 |
| 4,604,452 | 8/1986 | Shimp | 528/422 |
| 4,608,434 | 8/1986 | Shimp | 528/422 |
| 4,709,008 | 11/1987 | Shimp | 528/422 |
| 4,740,584 | 4/1988 | Shimp | 528/422 |
| 4,785,075 | 11/1988 | Shimp | 528/422 |
| 4,839,442 | 6/1989 | Craig, Jr. | 528/422 |
| 4,847,233 | 7/1989 | Shimp | 502/171 |
| 4,861,823 | 8/1989 | Qureshi | 528/422 |
| 4,999,699 | 3/1991 | Christie et al. | 528/422 |
| 5,002,818 | 3/1991 | Licari et al. | 428/209 |
| 5,077,319 | 12/1991 | Wang et al. | 521/89 |
| 5,150,195 | 9/1992 | Nguyen | 252/512 |
| 5,155,066 | 10/1992 | Nguyen | 437/209 |
| 5,186,880 | 2/1993 | Gaku et al. | 528/422 |
| 5,232,613 | 8/1993 | Bacon et al. | 252/8.6 |
| 5,338,594 | 8/1994 | Wang et al. | 428/117 |
| 5,358,992 | 10/1994 | Dershem et al. | 252/511 |
| 5,371,178 | 12/1994 | Nguyen | 252/514 |
| 5,386,000 | 1/1995 | Nguyen | 528/422 |

OTHER PUBLICATIONS

Shimp and Craig, "New Liquid Dicyanate Monomer for Rapid Impregnation of Reinforcing Fibers" 34th International Sampe Symposium, Reno, pp. 1326–1346 (1989).

Hi-tek Polymers, "AroCy Cyanate Ester Safety and Handling Bulletin" AroCy Safety and Handling (May 1989).

Shimp, D.A., "Thermal Performance of Cyanate Functional Thermosetting Resins" SAMPE Quarterly pp. 41–46 (Oct. 1987).

"AroCy L–10 Cyanate Ester Monomer" Rhone–Poulenc (4 pg. brochure) (Oct. 9, 1990).

Shimp et al., "AroCy Cyanate Ester Resins, Chemistry, Properties and Applications" Rhone–Poulenc Inc., Table of Contents & Introduction, pp. 1–9 and Bibliography, pp. 35–36 (May 1991).

*Primary Examiner*—Tae Yoon
*Attorney, Agent, or Firm*—Gray Cary Ware & Freidenrich; Stephen E. Reiter

[57] ABSTRACT

In accordance with the present invention, there are provided adhesive formulations containing small amounts of bleed control agent, which render the invention compositions extremely resistant to resin bleed. Several different types of bleed control agents are contemplated for use in the practice of the present invention, e.g., cationic surfactants, tertiary amines, tertiary phosphines, amphoteric surfactants, polyfunctional compounds, and the like, as well as mixtures of any two or more thereof.

33 Claims, No Drawings

1

BLEED RESISTANT CYANATE ESTER-CONTAINING COMPOSITIONS

This application is the U.S. National Stage of International application PCT/US96/04960, filed Apr. 11, 1996, now abandoned, which claims priority from U.S. patent application Ser. No. 08/475,006, now U.S. Pat. No. 5,646,241, filed Jun. 7, 1995, which is a continuation in part of U.S. patent application Ser. No. 08/439,975, filed May 12, 1995, now abandoned.

FIELD OF THE INVENTION

The present invention relates to adhesive compositions. In a particular aspect, the present invention relates to modified adhesive compositions having reduced propensity to bleed upon application to a substrate.

BACKGROUND OF THE INVENTION

Monomer vehicles used in die attach paste compositions tend to bleed out onto the substrate during cure, and even (in some cases) during room temperature staging of the adhesive. Indeed, resin bleed is a serious issue for die attach in electronic packaging. "Bleed" is defined herein as separation of the monomer vehicle phase and filler during staging or cure, resulting in spread of resin away from the die bond area. Resin bleed can generate wire bond non-sticks if it flows up onto bonding pads of the microelectronic device itself or the package into which it has been placed.

There are several potential impacts of this problem, e.g., a package assembler must deal with the likelihood of reduced product yields (and the attendant increased costs for manufacture), the part-to-part variability of the bleed phenomenom results in unacceptable part-to-part variability of the desired product, thereby necessitating the additional expense of 100% visual inspection of each component before being passed onto the wire bond step, and the like.

U.S. Pat. No. 4,483,898, issued to Harold Schonborn, et. al., and assigned to AT&T, discloses the use of alcohols, amides, amines, carboxylic acids, and esters containing two to twelve carbon atoms as allegedly being effective for the reduction of spreading of liquid films on substrates. The inhibition of resin bleed for epoxy, acrylate and silicone adhesive systems was the specific focus of this patent. The preferred bleed inhibiting compounds were poly-fluorinated (i.e. where most or all of the hydrogens of the hydrocarbon residue had been replaced by fluorine). The effective range contemplated by this patent is 0.05 to 5% by weight of the liquid phase. It is interesting to note, however, that the bleed control failed at 0.2% by weight of the most preferred bleed inhibiting agent in the absence of any "coupling agent" (see example VII). Furthermore, several of the compounds cited in '898 had deleterious effects on the pot life of the epoxy systems in which they were used (see, for example, Example VIII).

Accordingly, there is still a need in the art for compositions and methods useful for reducing the occurrence of resin bleed when die-attach compositions are applied to a substrate.

BRIEF DESCRIPTION OF THE INVENTION

In accordance with the present invention, we have discovered that the addition of small amounts of bleed control agent(s) to adhesive formulations renders such compositions extremely resistant to resin bleed. Several different types of bleed control agents are contemplated for use in the practice of the present invention, e.g., cationic surfactants, tertiary amines, tertiary phosphines, amphoteric surfactants, polyfunctional compounds, and the like, as well as mixtures of any two or more thereof.

DETAILED DESCRIPTION OF THE INVENTION

In accordance with the present invention, there are provided compositions for attaching a device to a substrate. Invention compositions comprise:

a monomer vehicle comprising at least one polycyanate ester monomer;

a quantity of a bleed control agent sufficient to reduce resin bleed upon application of said composition to a substrate; and optionally a metal catalyst.

Invention compositions can optionally contain filler material. Fillers contemplated for use in the practice of the present invention can be thermally and/or electrically conductive, and can be present in widely varying amounts, typically falling in the range of about 20 to about 92 wt. percent, based on the total weight of the attach paste.

Examples of electrically conductive fillers contemplated for use in the practice of the present invention include, for example, silver, nickel, cobalt, copper and aluminum fillers, as well as alloys of such metals. Both powder and flake forms of filler may be used in the attach paste compositions of the present invention. The preferred thickness of flake is under 2 microns with a dimension of about 20 to about 25 microns. Flake employed herein preferably has a surface area of about 0.15 to 5.0 $m^2/g$ and a tap density of 0.4 to 5.5 g/cc. Powder employed herein preferably has a diameter of about 0.5 to 15 microns.

Cyanate ester monomers contemplated for use in the practice of the present invention contain two or more ring forming cyanate (—O—C≡N) groups which cyclotrimerize to form substituted triazine rings upon heating. Because no leaving groups or volatile byproducts are formed during curing of the cyanate ester monomer, the curing reaction is referred to as addition polymerization. Suitable polycyanate ester monomers that may be used in the practice of the present invention include, for example, 1,1-bis(4-cyanatophenyl)methane, 1,1-bis(4-cyanatophenyl)ethane, 2,2-bis(4-cyanatophenyl)propane, bis(4-cyanatophenyl)-2,2-butane, 1,3-bis[2-(4-cyanato phenyl)propyl]benzene, bis(4-cyanatophenyl)ether, 4,4'-dicyanatodiphenyl, bis(4-cyanato-3,5-dimethylphenyl)methane, tris(4-cyanatophenyl)ethane, cyanated novolak, 1,3-bis[4-cyanatophenyl-1-(1-methylethylidene)]benzene, cyanated phenol-dicyclopentadiene adduct, and the like. Polycyanate ester monomers utilized in accordance with the present invention may be readily prepared by reacting appropriate dihydric or polyhydric phenols with a cyanogen halide in the presence of an acid acceptor.

Monomers that can optionally be combined with polycyanate ester monomer(s) in accordance with the present invention are selected from those monomers which undergo addition polymerization. Such monomers include vinyl ethers, divinyl ethers, diallyl ethers, dimethacrylates, dipropargyl ethers, mixed propargyl allyl ethers, monomaleimides, bismaleimides, and the like. Examples of such monomers include cyclohexanedimethanol monovinyl ether, trisallylcyanurate, 1,1-bis(4-allyloxyphenyl)ethane, 1,1-bis(4-propargyloxyphenyl)ethane, 1,1-bis(4-allyloxyphenyl-4'-propargyloxyphenyl)ethane, 3-(2,2-dimethyltrimethylene acetal)-1-maleimidobenzene, 2,2,4- trimethylhexamethylene-1,6-bismaleimide, 2,2-bis[4-(4-maleimidophenoxy)phenyl]propane, and the like.

Various monomers may be combined to obtain a liquid monomer vehicle, without the need for any added solvent/diluent, such as alkylphenol. For example, when 1,1-bis(4-cyanatophenyl)ethane, having a melting point of 29° C., and 2,2,4-trimethylhexamethylene-1,6-bismaleimide, having a melting point range of 75° to 125° C., were combined (in the absence of alkylphenol), mixtures containing up to 12 wt. percent bismaleimide were found to remain liquid indefinitely. The lowest melting mixture contained 8 wt. percent bismaleimide and had a melting point of 26.07° C., which is three degrees below the melting point of 1,1-bis(4-cyanatophenyl)ethane. The viscosity of this mixture was lower than that of the pure dicyanate ester. Surprisingly, the thermal stability of polymer derived from this mixture exceeded the thermal stability of the polycyanate ester homopolymer. Thermal stability was determined using thermogravimetric analysis run at a temperature ramp rate of 10° C./minute under an air purge. The decomposition onset temperature for the polymer derived from the mixture was 438° C., whereas the decomposition onset temperature for the homopolymer was 419° C.

Metal catalysts employed in the practice of the present invention are metal acetylacetonates which are metal chelates wherein the preferred metal is a transition metal. Examples of suitable metals employed herein are cobalt, manganese, tin, zinc, copper and nickel, all in the divalent state; manganese, iron, cobalt and aluminum, all in the trivalent state; and tetravalent titanium. The presently most preferred metal catalyst is cobalt(III) acetylacetonate. Typically, the metal catalyst is present in the range of about 50 to about 1500 ppm.

As employed herein, the term "bleed control agent" refers to a variety of additives which, acting alone or in combination, reduce and/or inhibit the propensity of monomer vehicle phase and filler to separate. Examples of the types of compounds contemplated for use in the practice of the present invetion as bleed control agents include cationic surfactants, tertiary amines, tertiary phosphines, amphoteric surfactants, polyfunctional compounds, and the like, as well as mixtures of any two or more thereof.

Those of skill in the art recognize that the quantity of bleed control agent employed in the practice of the present invention can vary widely, typically falling in the range of about 0.1 up to about 10 wt % of the organic fraction of the cyanate ester-containing composition (i.e., the unfilled organic vehicle).

Additives contemplated for use in the practice of the present invention include higher molecular weight, tetravalent nitrogen compounds (where the nitrogen atom bears a positive charge). Examples of such compounds include quaternary ammonium salts where the hydrocarbon residues attached to the nitrogen comprise linear alkyl, branched alkyl, linear alkenyl, branched alkenyl, benzyl, cycloaliphatic, ethyl hydroxy, propyl hydroxy, polyalkylene oxide and phenyl substituted alkyl groups. The nitrogen, furthermore, may be incorporated into a cyclic structure such as a pyridine, a piperazine, a piperidine, a pyrazine, a pyrimidine, a quinoline, an isoquinoline, an imidazole, and the like, or any substituted analogs thereof. The counter ion for the quaternized ammonium cation may be any anion other than fluoride or chloride. The counter ion may also be covalently linked to the nitrogen by a carbon containing bridging group as in the case of betaines, sulfobetaines, N-alkylaminopropionic acids, N-alkyl-iminodipropionic acids, imidazoline carboxylates, tertiary amine oxides and tertiary phosphine oxides (i.e. amphoteric, or zwitterionic surfactants).

Cationic surfactants contemplated for use in the practice of the present invention include quaternary onium compounds (e.g., quaternary ammonium compounds, quaternary phosphonium compounds, or mixtures of any two or more thereof). Preferably, quaternary onium compounds employed in the practice of the present invention have in the range of about 15 up to about 100 total carbon atoms, with quaternary onium compounds wherein at least one side chain thereof is at least 12 carbon atoms in length being especially preferred.

Those of skill in the art recognize that the quantity of cationic surfactant employed in the practice of the present invention can vary widely. Typically, the quantity of cationic surfactant falls in the range of about 0.1 up to 3 wt % of the organic fraction of said cyanate ester-containing composition.

Exemplary quaternary ammonium compounds include distearyldimethylammonium salts, hexadecylpyridinium salts, hexadecyldimethylphenylammonium salts, decyltrimethylammonium salts, dodecyltrimethylammonium salts, tetradecyltrimethylammonium salts, hexadecyltrimethylammonium salts, octadecyltrimethylammonium salts, eicosyltrimethylammonium salts, behenyltrimethylammonium salts, oleyltrimethylammonium salts, dioleyldimethylammonium salts, trioleylmethylammonium salts, didecyldimethylammonium salts, didodecyldimethylammonium salts, ditetradecyldimethylammonium salts, dihexadecyldimethylammonium salts, dioctadecyldimethylammonium salts, dieicosyldimethylammonium salts, dibehenyldimethylammonium salts, tridecylmethylammonium salts, tridodecylmethylammonium salts, tritetradecylmethylammonium salts, trihexadecylmethylammonium salts, trioctadecylmethylammonium salts, trieicosylmethylammonium salts, tribehenylmethylammonium salts, oleylhydroxyethyl imidazoline, and the like, as well as mixtures of any two or more thereof.

Presently preferred cationic surfactants include quaternary ammonium compounds where the sum of the alkyl groups adds up to at least twenty carbons and at least one of the hydrocarbon residues contains twelve or more carbons —ideally, where the sum of the carbon residues bonded to the central nitrogen is at least thirty-four and at least one of the hydrocarbon residues contains sixteen or more carbons.

Exemplary quaternary phosphonium compounds include tributylhexadecylphosphonium salts, hexadecyltriphenylphosphonium salts, and the like, as well as mixtures of any two or more thereof.

Tertiary amines contemplated for use in the practice of the present invention include tertiary amines having in the range of about 18 up to about 100 total carbon atoms. Preferably, at least one side chain of said tertiary amine is at least 16 carbon atoms in length.

Tertiary phosphines contemplated for use in the practice of the present invention include tertiary phosphines having in the range of about 18 up to about 100 total carbon atoms. Preferably, at least one side chain of said tertiary phosphine is at least 16 carbon atoms in length.

Those of skill in the art recognize that the quantity of tertiary amine and/or tertiary phosphine employed in the practice of the present invention can vary widely, typically falling in the range of about 0.1 up to 5 wt % of the organic fraction of said cyanate ester-containing composition.

Exemplary tertiary amines contemplated for use in the practice of the present invention include hexadecyldimethylamine, dihexadecylmethylamine, octadecyldimethylamine, dioctadecylmethylamine, dimethylbehenylamine, dimethyleicosylamine, N,N,N'- trimethyl-N'-hexadecyl-1,2-diaminoethane, N,N,N'-trimethyl-N'-octadecyl-1,2-diaminoethane, N,N,N'-trimethyl-N'-eicosyl-1,2-diaminoethane, N,N,N'-trimethyl-N'-behenyl-1,2-diaminoethane, N,N,N¹,N'-tetramethyl-1,20-diamino-(10,11-dioctyl)eicosane, and the like, as well as mixtures of any two or more thereof.

Exemplary tertiary phosphines contemplated for use in the practice of the present invention include hexadecyldimethylphosphine, dihexadecylmethylphosphine, octadecyldimethylphosphine, dioctadecylmethylphosphine, dimethylbehenylphosphine, dimethyleicosylphosphine, N,N,N'-trimethyl-N'-hexadecyl-1,2-diphosphinoethane, N,N,N'-trimethyl-N'-octadecyl-1,2-diphosphinoethane, N,N,N'-trimethyl-N'-eicosyl-1,2-diphosphinoethane, N,N,N'-trimethyl-N'-behenyl-1,2-diphosphinoethane, and the like, as well as mixtures of any two or more thereof.

Amphoteric surfactants contemplated for use in the practice of the present invention include higher alkyl betaines, higher alkyl sulfobetaines, N-alkylaminopropionic acids, N-alkyliminodipropionic acids, imidazoline carboxylates, tertiary amine oxides, tertiary phosphine oxides, and the like, as well as mixtures of any two or more thereof.

Those of skill in the art recognize that the quantity of amphoteric surfactant employed in the practice of the present invention can vary widely, typically falling in the range of about 0.1 up to 2 wt % of the organic fraction of said cyanate ester-containing composition.

The presently preferred amphoteric surfactants for use in the practice of the present invention include higher alkyl betaines and higher alkyl sulfobetaines. An exemplary higher alkyl betaine is palmitamidopropyl betaine.

Exemplary higher alkyl sulfobetaines include isostearylamidopropylethyldimonium ethosulfate, cocodimethylammonium-3-sulfopropyl betaine, lauryldimethylammonium-3-sulfopropyl betaine, myristyldimethylammonium-3-sulfopropyl betaine, palmityldimethylammonium-3-sulfopropyl betaine, stearyldimethylammonium-3-sulfopropyl betaine, tallowdimethylammonium-3-sulfopropyl betaine, distearylmethylammonium-3-sulfopropyl betaine, cocoamidopropyldimethylammonium-3-sulfopropyl betaine, tallowamidopropyldimethylammonium-3-sulfopropyl betaine, and the like, as well as mixtures of any two or more thereof.

The rate of bleed of a cyanate ester adhesive on a substrate is strongly affected by temperature. The bleed rate for freshly dispensed adhesive at room temperature is usually extremely slow (although not zero). The curing process, however, requires a thermal excursion in order to develop the thermoset properties of the paste. The adhesive also generates additional heat during the cure exotherm. The cure of cyanate esters is particularly exothermic (approximately 700 joules per gram—depending on the equivalent weight of the cyanate used). As a consequence of this heating, the initial stages of cure result in a marked drop in the viscosity of the cyanate ester monomer. The viscosity of the adhesive falls to a minimum just before the adhesive attains the gel point. Since the rate of bleed is accelerated when the fluid phase of the adhesive is at a low viscosity, one potential means to achieve resin bleed reduction is to speed the transition to the gel point. An increase in the rate of cure, therefore, would represent a reduction in the time window during which bleed is most likely to occur.

Polyfunctional compounds that can directly interact with (i.e., work in concert with) the cyanate ester monomer, or independently cure (to form a cross-linked network) in the presence of the cyanate ester monomer during the initial stages of cure would provide an opportunity to reduce bleed by accelerating the rate of crosslinking. For this purpose, compounds bearing a plurality of functional groups such as acrylates, methacrylates, hydroxyls, cyanates, maleimides, allyls, epoxies, and the like, as well as combinations thereof, can be employed.

For example, a polyfunctional cyanate would potentially offer the advantage of reduced gel times for the cyanate monomer system without introducing any new functionality to the thermoset cure. Three grades of polyfunctional cyanate ester oligomers (with anywhere from approximately three to nine cyanate functions per molecule) are available from Lonza Inc., Fair Lawn, N.J., under the designation of "Primaset PT Resins".

Another class of polyfunctional compounds that can be used to decrease the time required to attain the gel point includes polyvinyl compounds. The most preferred polyvinyl compounds are the esters of acrylic or methacrylic acid. It is desirable that these monomers contain at least two polymerizable functions per molecule. These monomers are generally soluble in or miscible with liquid cyanate ester blends. Examples of such monomers include bisphenol A dimethacrylate, bisphenol A bis(2-hydroxypropyl) methacrylate, 1,6-hexanediol dimethacylate, 1,10-decanediol dimethacylate, pentaerythritol triacrylate, trimethylolpropane trimethacrylate, tris (2-hydroxyethyl) isocyanurate trimethacrylate, pentaerythritol tetraacrylate, di-trimethylolpropane tetraacrylate, dipentaerythritol pentaacrylate, and the like. These molecules may be rapidly polymerized to generate a cross-linked network.

When polyvinyl compounds as described above are used, it is desirable to add a free radical catalyst to insure the proper cure of these monomers. It is furthermore desirable to select a catalyst that has a very low temperature onset for the generation of free radicals. Examples of such low-temperature free radical catalysts include benzoyl peroxide, diisononanoyl peroxide, lauroyl peroxide, di-(2-ethylhexyl) peroxydicarbonate, di-(4-tert-butylcyclohexyl) peroxydicarbonate, dimyristyl peroxydicarbonate, t-amyl peroxy-2-ethylhexanoate, and the like.

The acrylate and/or methacrylate monomers described herein do not co-cure with the cyanate ester constituents of the adhesive, but rather cure independently. The final thermoset, in this case, comprises an interpenetrating network of polyacrylate/methacrylate within the cyclotrimerized cyanate matrix. Surprisingly, the incorporation of as much as twenty weight percent of these monomers has been found to have little or no effect on the thermal decomposition onset temperature (measured via thermogravimetric analysis) for the cured adhesive.

The presently most preferred, non-cyanate, functional group is hydroxyl. Polyhydroxy functionalized compounds are capable of rapid reaction with cyanate functions to form (thermally reversible) imidocarbonate linkages according to Scheme I:

$$-C_6H_4-OC\equiv N + -ROH \longrightarrow -C_6H_4-\overset{\overset{NH}{\|}}{OC}-OR \quad I$$

Furthermore, imidocarbonates are believed to accelerate the rate of cyclotrimerization of cyanate monomers themselves. The presence of several reactive sites in the same molecule enhances cross linking and, therefore, the rate of viscosity increase during the early stages of cure.

It is highly desirable, when the polyfunctional compounds used have hydroxyl functional groups, they should also have little or no solubility in the cyanate ester monomer at room temperature. This property insures that the additive will have no deleterious effect on the potlife of the adhesive. One particularly useful additive having all of the desirable properties set forth herein is poly(4-hydroxystyrene) (PHS). A room temperature solubility test was run that consisted of suspending five percent by weight of finely powdered PHS in a room-temperature-stable, 85:15 liquid blend of 1,1-bis (4-cyanatophenyl)ethane (Arocy L-10 from Ciba) and 2,2-bis(4-cyanatophenyl)propane (Arocy B-10 from Ciba). The particle size distribution for the original powdered PHS was compared to the one obtained for the PHS that had been sitting in the liquid cyanate monomer blend for one week at room temperature. The average particle size for the original powder was 8.8 micrometers with a minimum and maximum particle size measured at 1.8 and 68.5 micrometers, respectively. The cyanate ester immersed particles had an average diameter of 6.5 micrometers along with maximum and minimum measurements at 1.8 and 66.1 micrometers, respectively. It was concluded from this that neither swelling nor significant dissolution of the PHS particles occurred during room temperature storage. It is also noteworthy that there was no detectable change in the viscostity of the cyanate monomer vehicle containing the powdered PHS after one week storage at room temperature.

It is believed that the PHS swells and/or dissolves significantly only upon heating. The cure acceleration property, therefore, was presumed to be dependent upon the PHS particle size present in the cyanate ester. Finer particles, therefore, should have a more pronounced accelerating affect on cure of the cyanate monomers. A test was conducted to determine the dependence of the gel time on the PHS particle size (see Example 1).

Additional polyfunctional compounds contemplated for use in the practice of the present invention include pentaerythritol, poly[glycidyl (meth)acrylate], polyvinyl alcohol, poly[2-hydroxyethyl (meth)acrylate], sucrose monostearate, sorbitan monooleate, 1,1,1-tris (hydroxymethyl)ethane, polyglycerol monooleate, polyglycerol dioleate, and the like, as well as mixtures of any two or more thereof.

Those of skill in the art recognize that the quantity of polyfunctional compound employed in the practice of the present invention can vary widely, typically falling in the range of about 0.5 up to 10 wt % of the organic fraction of said cyanate ester-containing composition.

The presently preferred polyfunctional compounds used to increase the rate of viscosity rise during cure include novolac resins, poly(4-hydroxystyrene), poly(2-hydroxyethyl methacrylate), poly(2-hydroxypropyl methacrylate), and the like. The preferred reactive lubricant includes 12-hydroxystearic acid.

An especially preferred polyfunctional compound contemplated for use in the practice of the present invention is poly(4-hydroxystyrene) (PHS). Typically, PHS contemplated for use in the practice of the present invention has a molecular weight in the range of about 1,000 up to 1,000,000.

Those of skill in the art recognize that it may be desirable to incorporate one or more conventional additives in to compositions of the invention. Examples of such additives include, for example, organic or inorganic fillers (e.g., fumed silica), certain antioxidants, polymerization inhibitors, plasticizers, and the like. Conversely, it is also recognized by those of skill in the art, based on the intended use of invention compositions for die attach, that the incorporation of certain types of additives is clearly not desirable, such as, for example, additives which would lead to the formation of voids (which compromise the adhesion, thermal conductivity, etc. of invention compositions). A particular additive which is not contemplated for use herein is blowing agents, which release gas upon cure of the composition, thus introducing undesirable voids into the resulting cured die attach composition.

Thus, for example, incorporation of a small amount of fumed silica may be beneficial in that it may aid in reducing the amount of liquid bleed that can occur during the curing process. Specifically, introduction of fumed silica aids in reducing the amount of uncured monomer that wicks out onto the substrate. Minimizing liquid bleed is desirable since excessive spread of monomer can result in contamination of the die being attached to the substrate. The addition of a small amount of fumed silica can also be used to increase the thixotropic index of a paste. This effect is particularly important when low surface area metal fillers are employed in an attach paste. In the absence of fumed silica, such a paste composition may give a "taily dispense", a term referring to a paste that does not break off cleanly from an automatic dispensing head. This results in a tail of paste dragging across a component during the assembly process, which may make the component unusable. When fumed silica is incorporated in the paste compositions of the invention, the amount will vary from about 0.2 wt. percent to about 2 wt. percent.

It is well known to those skilled in the art that the thermo-oxidative stability of a high temperature polymer can be improved by the incorporation of an antioxidant. Use of an antioxidant in paste compositions containing high temperature polymers and finely divided silver can be very beneficial. Silver metal can act as an oxidation catalyst and contribute to early thermal degradation. This effect is especially evident when the filler employed is a high surface area silver powder. Moreover, the severity of the problem increases as the solids loading of silver powder increases. For example, thermal degradation onset for a paste loaded with 85 wt. percent silver powder is about 390° C. A paste made with identical ingredients loaded by only 80 wt. percent silver powder had a decomposition onset around 400° C. It is desirable to be able to load the silver content as high as possible in order to obtain the highest possible thermal and electrical conductivity. Incorporation of from about 0.5 to about 1.0 wt. percent antioxidant can substantially improve the thermal stability of attach paste compositions containing silver powder. The onset of thermal decomposition for an attach paste containing 85 wt. percent silver powder and 0.5 wt. percent antioxidant was 410° C. The onset for thermal decomposition of a control paste containing no antioxidant was approximately 20° C. lower. Antioxidants that are suitable for use in invention compositions include, for example, 4,4'-dioctyldiphenylamine, 3,3'diethyl-5,5'-dinonyldiphenyl amine, and the like.

In accordance with another embodiment of the present invention, there are provided compositions for attaching a device to a substrate. Invention compositions comprise:
  monomer vehicle comprising at least one polycyanate ester monomer;
  filler; and
  a quantity of a bleed control agent sufficient to reduce resin bleed upon application of said composition to a substrate.

In accordance with still another embodiment of the present invention, there are provided methods for reducing resin bleed of cyanate ester-containing compositions upon application to a substrate. Invention methods comprise adding to cyanate ester-containing compositions a quantity of a bleed control agent sufficient to reduce resin bleed upon application of the resulting composition to a substrate.

Without wishing to be bound by any theory, it is believed that the major issues that impact resin bleed include the following:

1) Cleanliness of the substrate.
2) Surface roughness of the substrate.
3) Surface energy of the substrate.
4) Viscosity of the adhesive.
5) Surface tension of the adhesive vehicle.
6) Cure rate of the adhesive.

The first two factors identified above are beyond the control of the adhesive formulator. In accordance with the present invention, however, it has been found that various compositional modifications can have an impact on the remaining four issues. The following strategies, applied alone or in combination, provide a significant reduction and/or total elimination of resin bleed.

1) Addition of a small, but effective, amount of a cationic surfactant.
2) Addition of a small, but effective, amount of a compound capable of forming a cationic surfactant in situ.
3) Addition of a small, but effective, amount of an amphoteric surfactant.
4) Addition of a poly-functional compound that is capable of participating in a rapid, thermally initiated, reaction with the monomer vehicle.
5) The combination of stratagies (1), (2) or (3) listed above with strategy number (4).
6) The preparation of silver flake coated with a lubricant that has residual functionality capable of reacting with the monomer vehicle.

Presumably, resin bleed inhibition is a function of the formation of a continuous or semi-continuous film of the lubricant on the substrate surface. It is believed that this film significantly reduces the apparent surface energy of the substrate and thus reduces the driving force for the adhesive liquid phase to wet the surface.

It has been observed herein that the most effective bleed control agents are those that contain one or more higher alkyl substituents. The preferred hydrocarbon chain length is at least twelve carbons and the most preferred is at least sixteen carbons in length.

It appears that the higher alkyl chains also are harder to displace off of the substrate surface than their lower alkyl analogs. That is to say, the higher alkyl substituted quaternary ammonium compounds have an exemplary carboxylic acid from '898 would decarboxylate. The resulting monohydro-perfluorooctane would likewise be extremely prone toward elimination of hydrogen fluoride. The consequences of this would be disastrous for the reliability of the microelectronic device since the fluoride ion is considered to be extremely corrosive toward aluminum circuitry in the presence of even trace moisture conditions. Furthermore, it is not necessary that any of these fluoride ion generating reaction steps be very efficent since the quantity of this ion that can be tolerated is extremely low. The specification limit in the industry for water extractable fluoride ion is less than ten parts per million.

The invention will now be described in greater detail by reference to the following non-limiting examples.

EXAMPLE 1

Effect of particle size of polyfunctional compound on resin bleed

The base thermoset vehicle employed for the experiments summarized in Table 1 comprises a liquid cyanate ester mixture (i.e., an 85:15 mixture of L-10:B-10, i.e., 1, 1-bis (4-cyanatophenyl)ethane and 2.2-bis(4-cyanatophenyl) propane, respectively) and 500 ppm (metals basis) of cobalt (III) acetylacetonate catalyst. Five percent by weight of various sieved fractions of poly(hydroxy styrene) (PHS) were added to this vehicle. The sieve fractions employed were −170 +270, −270 +−325, −325 +500 and −500 mesh.

A gel point test was conducted by placing a 30.3±0.2 milligrams drop of each of the test compositions on 22×22 millimeter borosilicate microscope cover slips and then heating these samples on a hot plate fixed at various temperatures. The gel point, recorded according to equilibrium concentration gradient strongly shifted toward the substrate surface.

Another advantage of cationic surfactants (e.g., quaternary ammonium compounds) over several of the compound types found in the prior art is the absence of reactivity with the monomers used in commercially important adhesive systems. For example, with the most preferred bleed inhibitors cited in U.S. Pat. No. 4,483,898 (i.e., perfluorooctanoic acid and 1H,1H-pentadecafluoro octylamine), the carboxylic acid function is capable of rapid reaction with many of the most common monomers used in die attach adhesives (including cyanate esters, cycloaliphatic epoxies, and glycidyl ether epoxies). The amine cited in '898 is even more reactive with epoxies and cyanates (e.g. the addition of a primary aliphatic amine to a cyanate ester at room temperature results in an instantaneous—almost explosive—reaction). This reactivity would have an obvious deleterious effect on the pot life of a cyanate ester adhesive system.

A significantly more serious limitation to the preferred exemplary compounds cited in '898 is the propensity of such compounds to generate fluoride ion contamination in the cured adhesive. The described amine compound has hydrogen residues vicinyl to (i.e. on a carbon immediately adjacent to) covalently bound fluorine. Such compounds are well known to be capable of eliminating hydrogen fluoride (HF). Elimination of HF would, in turn, generate significant quantities of silver fluoride in the presence of any silver oxide residues on a silver filler according to Scheme II:

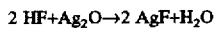

It is also very likely that under realistic use conditions (e.g. during cure and/or lid seal heating cycles) that the this test, represented the first instant in time when a solid probe would no longer penetrate the surface of the sample drop. The results of that test are summarized in Table 1.

TABLE 1

| Gel time (seconds) as a function of PHS particle size | | | | | |
|---|---|---|---|---|---|
| | PHS particle size, mesh | | | | |
| Temperature (°C.) | −170 +270 | −270 +325 | −325 +500 | −500 | Control Vehicle |
| 150 | 405 | 380 | 355 | 325 | 1220 |
| 160 | 140 | 189 | 127 | 125 | 340 |
| 170 | 68 | 80 | 70 | 65 | 255 |
| 180 | 29 | 29 | 31 | 21 | 90 |

TABLE 1-continued

Gel time (seconds) as a function of PHS particle size

| Temperature (°C.) | PHS particle size, mesh | | | | Control Vehicle |
|---|---|---|---|---|---|
| | −170 +270 | −270 +325 | −325 +500 | −500 | |
| 200 | 14 | 17 | 13 | 16 | 24 |
| 215 | 13 | 13 | 11 | 11 | 21 |

It is apparent from these results that the gel point time is significantly shorter, at every test temperature, for all of the PHS-containing samples, relative to the control. What appeared to be a cure-rate-dependence on particle size was clear-cut for only the lowest temperature run. The compositions that contained the finer particle size distributions generally did have enhanced cure rates despite the presence of some striking anomalies. Differences in cure rates for the various samples were diminished at the highest cure temperatures.

EXAMPLE 2

Effect of other polyfunctional compounds on resin bleed

Other polyfunctional compounds (besides PHS) were also investigated for their impact on cure time. Gel point measurements were made for all of these materials at a 5% by weight loading in the base vehicle described in Example 1. 0.5% of di-(4-tert-butylcyclohexyl) peroxydicarbonate free radical catalyst was also included in each of the compositions containing acrylate monomers. The cure temperature was fixed at 180°±2° C. Solid samples were sieved to −270 mesh and liquid samples were simply added to the base formulation neat. The results of this gel point testing are summarized in Table 2.

TABLE 2

Gel Point Times for Several Polyfunctional Additives

| Designation | Compound | Gel Point Time (seconds) |
|---|---|---|
| 2A | Poly(gylcidyl methacrylate) | 85 |
| 2B | Poly(vinyl alcohol) | 85 |
| 2C | Poly(2-hydroxyethyl methacrylate) | 44 |
| 2D | Sucrose monostearate | 50 |
| 2E | Sorbitan monooleate | 58 |
| 2F | 1,1,1-tris (hydroxymethyl) ethane | 80 |
| 2G | Polyglycerol monooleate | 35 |
| 2H | Polyglycerol dioleate | 57 |
| 2I | Poly(4-hydroxystyrene) | 35 |
| 2J | Primaset PT30 | 64 |
| 2K | Pentaerythritol tetraacrylate | 18 |
| 2L | Pentaerythritol triacrylate | 14 |
| 2M | Control Vehicle | 90 |

At the loading levels employed, and with this particular base formulation, the cure rate increase for the poly(glycidyl methacrylate) and the poly(vinyl alcohol) additives appeared to be insignificant, relative to control. In contrast, use of the polyfunctional cyanate (Primaset PT 30; 2J) did have a significant impact on the cure rate. One attractive feature inherent to this gel rate enhancer is that no new functionality is introduced to the system. The six most impressive cure rate accelerants in this test were pentaerythritol triacrylate (2L), pentaerythritol tetraacrylate (2K), polyglycerol monooleate (2G), poly(4-hydroxystyrene) (2I), poly(2-hydroxyethyl methacrylate) (2C), and sucrose monostearate (2D). Of these, the polyglycerol monooleate would not be particularly preferred due to a propensity to undergo a gel-like phase separation within minutes of mixing, and also since the room temperature stability for formulations containing this additive was not particularly high (the same phenomenon (i.e., relatively low room temperature stability) was also observed with the polyglycerol dioleate-containing formulation). No apparent viscosity change occurred with any of the other samples in this test after several days storage at room temperature.

The gel point recorded for the acrylate containing systems was totally a function of the free radical cure of these added (non-cyanate) monomers. Both of these samples (i.e., 2K and 2L) formed a gel network with extreme rapidity. There was, however, some syneresis (i.e., a thin film of uncured cyanate exuded out to the surface of the initially formed gel).

EXAMPLE 3

Addition of More Reactive Cyclotrimerization Catalysts for Bleed Control

It is well known to those of skill in the art of cyanate ester chemistry that certain transition metal cure catalysts are more reactive than others in promoting cyclotrimerization of cyanate ester monomers. An increase in the reaction rate would reduce the time required for the development of a gel network once cure is commenced. Metal carboxylates and/or acetylacetonates (AcAcs) that are noted for high rates of cure include zinc(II), copper(II), silver(I), iron(III), manganese(II) and (III), and nickel(II). The most preferred among these is Cu(II), in part, because it does not promote hydrolysis of the cyanate ester (either in the pre-cured or cured state).

Accordingly, a test was conducted to determine what effect the substitution of copper(II) acetylacetonate (Cu(II) AcAc) for cobalt(III) acetylacetonate (Co(III)AcAc) would have on resin bleed. Paste compositions were prepared that contained 80% by weight silver flake in a cyanate ester monomer vehicle. The silver flake consisted of a blend of 68.2% SF84 (Degussa-Metz), 20.4% EA0095 and 11.4% EA0018 (both from Chemet corporation). The cyanate ester monomer mixture used consisted of 85% Arocy L-10 and 15% Arocy B-10 (both from Ciba-Geigy Corporation). Two separate cyanate ester vehicles were prepared by dissolving 500 parts per million (metals basis) of either Cu(II)AcAc or Co(II)AcAc into the combined cyanate monomers. The silver blend described above was then thoroughly mixed with each of the cyanate ester vehicles to create the two paste mixtures used in this experiment.

A gold plated coupon was fired at 350° C. to remove any organic residue (a process which had previously been shown to maximize bleed). Three equal sized (approximately 100 milligrams each) drops of the test paste (i.e., Cu catalyzed) were placed on the clean gold plated coupon as well as one drop of the control (Co catalyzed) paste. The part was then placed in a 150° C. oven for twenty minutes. Resin bleed was determined for each test spot. The bleed on the control paste was severe (approximately 187 mils). The maximum measured bleed for each of the test drops was 0 mils, 15 mils and 45 mils, respectively. Thus, the worst case bleed measured for the Cu(II)AcAc catalyzed composition was less than a quarter of that of the Co(III)AcAc catalyzed control.

Even though the above example utilized copper(II) as the sole transition metal catalyst, any of the transition metal catalysts mentioned above, or mixtures of the same, would have a similar effect on bleed. Experience with the cyanate ester combination employed herein suggests that 500 ppm Cu catalyst (as the acetylacetonate) represents the preferred upper concentration limit for this metal. Higher than 500 ppm Cu(II)AcAc reduces the usable room temperature pot life of the final pastes to less than sixteen hours. It is also preferable to use the acetylacetonate rather than a copper metal carboxylate (especially toward the upper concentration limit) since the former has been reported to posses superior latent cure characteristics.

EXAMPLE 4

Screening of additional potential bleed control agents

A screening test was conducted to determine what properties are most important for bleed control agents. Mixtures were made in which 0.5% by weight of each test compound was added to a liquid cyanate ester-containing control vehicle as described above in Example 1 (i.e., comprising an 85:15 mixture of L-10:B-10 and 500 ppm cobalt catalyst [on a metals basis--from Co(III)AcAc]).

A small droplet of each test mixture was carefully weighed onto a clean gold plated coupon (all coupons used had been fired through a 350° C. belt furnace profile under a nitrogen atmosphere, and all parts that had been subjected to this cleaning step were used within eight hours of firing). The weight of sample deposited for each mixture test was 0.7±0.1 milligram. All samples were cured on a hot plate, set at 190°±2° C., until the gel point had been attained. The diameter of the bleed region was measured on the cured samples and an approximate area of bleed was calculated based on this diameter. All bleed areas were then normalized with respect to the bleed measured for the control mixture (i.e. the bleed area deteriminied for each sample was divided by the bleed area of the control mixture and this fraction was then multiplied by 100 to derive an area percent indexed against the control mixture). Table 3 summarizes the results from this test.

TABLE 3

Relative Bleed for Cyanate Ester Additives On Gold Coupons

| Designation | Additive | Relative Area |
|---|---|---|
| 3A | None (control) | 100 |
| 3B | Dimethyldioctadecylammonium bromide | 1.9 |
| 3C | Dimethyloctadecylamine oxide | 68 |
| 3D | Perfluorooctanoic acid | 8.4 |
| 3E | Tributylhexadecylphosphonium bromide | 4.7 |
| 3F | Dioctadecylmethylammonium-3-sulfopropylbetaine | 30 |
| 3G | Hexadecyltriphenylphosphonium bromide | 66 |
| 3H | Tridodecylmethylammonium Iodide | 59 |
| 3I | Hexadecylpyridinium chloride monohydrate | 13 |
| 3J | Dodecylhexadecyldimethyl-ammonium iodide | 66 |
| 3K | Tetrabutylammonium bromide | 110 |
| 3L | Tetrabutylammonium borohydride | 100 |
| 3M | Dodecyldimethyloctadecylammonium iodide | 2.1 |
| 3N | Dimethyldioctadecylammonium cyanate | 41 |
| 3O | Dimethyldioctadecylammonium nitrate | 81 |
| 3P | Trimethylamine oxide dihydrate | 73 |
| 3Q | Perfluorooctanesulfonic acid tetrabutylammonium salt | 66 |
| 3R | Dodecyldimethylammonium-3-sulfopropylbetaine | 27 |
| 3S | Dimethyloctadecylammonium-3-sulfopropylbetaine | 2.4 |
| 3T | 1-(3-sulfopropyl)-2-vinylpyridinium betaine | 120 |
| 3U | Dimethylmethacryloxyethylsulfo-propylammonium betaine | 100 |
| 3V | N,N-dimethyloctadecylamine | 3.3 |
| 3W | Dodecyltrimethylammonium chloride | 7.6 |
| 3X | Dimethyldioctadecylammonium chloride | 21 |
| 3Y | N,N-dimethylhexadecylamine | 6.8 |
| 3Z | Tridodecylamine | 64 |
| 3AA | Trioctylphosphine oxide | 100 |
| 3BB | Triisooctylamine | 92 |
| 3CC | Dioctadecylmethylamine | 46 |
| 3DD | N,N-dimethyl-N-stearylamido-propylammonium-3-sulfopropylbetaine | 83 |
| 3EE | Tetronic 90R4 (BASF) | 46 |
| 3FF | Tetronic 904 (BASF) | 46 |
| 3GG | Tetronic 1107 (BASF) | 59 |
| 3HH | Triphenylphosphine | 83 |
| 3II | N,N-(2-hydroxyethyl)octadecyl amine | 67 |
| 3JJ | N,N-(2-hydroxyethyl)behenylamine | 109 |
| 3KK | N-behenylpiperidine | 67 |
| 3LL | Tribenzylamine | 29 |
| 3MM | Pefluorotributylamine | 46 |
| 3NN | 1H,1H-perfluorooctylamine | 30 |
| 3OO | N-Octadecylpyridinium iodide | 41 |
| 3PP | N-behenylpyridinium bromide | 3.5 |
| 3QQ | N,N'-dioctadecyl-N,N,N',N'-tetramethyl-1,2-ethanediamine diiodide | 21 |
| 3RR | N,N,N-triethyl-N-behenylammonium bromide | 30 |
| 3SS | N,N-dimethyl-N-hexadecyl-N-perfluorooctylammonium iodide | 30 |
| 3TT | Perfluorooctanesulfonic acid | 6.1 |
| 3UU | T-Carboxypropyl-polydimethyl-siloxane (PS402-United Chemical Technologies, Bristol, PA) | 30 |
| 3VV | N,N,N',N'-tetramethyl-1,20-diamino-(10,11-dioctyl)-eicosane | 2.6 |

Most of the additives tested herein had a significant impact on resin bleed reduction in this experiment. Six of the test compounds, however, were found to have substantially no effect. Two of these, 3T (i.e., 1-(3-sulfopropyl)-2-vinylpyridinium betaine) and 3U (i.e., dimethylmethacryloxyethylsulfo-propylammonium betaine) appeared to be completely insoluble in the liquid cyanate ester vehicle. 3L (i.e., tetrabutylammonium borohydride) produced an immediate color change in the cyanate/catalyst mixture (presumably, this color change had something to do with a chemical interaction (i.e. probably reduction/oxidation) between the cobalt catalyst and the borohydride anion). While no specific observations were made that would account for why 3K (i.e., tetrabutyl ammonium bromide) and 3AA (i.e., trioctylphosphine oxide) were ineffective, it is believed that there is a minimum hydrocarbon segment length necessary to achieve effective bleed control, and the butyl and octyl substituents present in 3K and 3AA, respectively, are below this threshold.

The most effective bleed control additives included 3B, 3D, 3E, 3I, 3M, 3R, 3S, 3V, 3W, 3X, 3Y, 3PP, 3QQ, 3TT and 3VV (i.e., dimethyldioctadecylammonium bromide, perfluorooctanoic acid, tributylhexadecylphosphonium bromide, hexadecyl pyridinium chloride monohydrate, dodecyldimethyl octadecylammonium iodide, dodecyldimethylammonium-3-sulfopropylbetaine, dimethyloctadecylammonium-3-sulfopropylbetaine, N,N-dimethyloctadecylamine, dodecyltrimethylammonium chloride, dimethyldioctadecylammonium chloride, N,N-dimethylhexadecylamine, N-behenylpyridinium bromide, N,N'-dioctadecyl-N,N,N',N'-tetramethyl-1,2-ethanediamine diiodide, perfluorooctanesulfonic acid and N,N,N',N'-tetramethyl-1,20-diamino-(10,11-dioctyl)-eicosane, respectively). The bleed area observed for these samples were all well under thrity percent of that of the control. Two of these materials (3W and 3X) are quaternary ammonium chlorides. While chloride ion containing compounds would be unacceptable in products intended for use in electronic packaging, additives 3W and 3X are clearly seen to be effective for bleed control, and could readily be used in other (i.e., non-electronic) applications.

All of the highly effective bleed control compounds noted above, with the exception of 3D, 3V, 3Y, 3TT and 3VV are quaternary compounds with one or more hydrocarbon segment lengths of at least twelve carbon atoms. The tertiary amines (3V, 3Y and 3VV) also have a higher alkyl (C-16 or C-18 or higher) hydrocarbon residue. It is likely that tertiary amines are "quaternized" in situ by reaction with the low (but significant) levels of phenolic species known to exist in commercially available preparations of L-10. Tertiary amines are strong Lewis bases and would be readily protonated in the presence of a phenol. A reaction scheme for the in situ quaternization of tertiary amines by phenolic residues is shown in Scheme III:

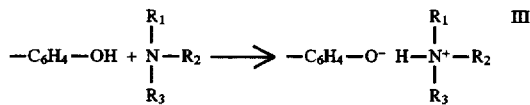

It is furthermore believed that unhindered (specifically, dimethylalkyl) tertiary amines (e.g., 3V, 3Y and 3VV) perform better since the in situ formation of quaternary ammonium compounds is much more facile in the absence of stearic interference. Additives 3D, 3Z, 3BB, 3MM and 3NN are cited in U.S. Pat. No. 4,483,898 (discussed above). Compound 3D is the only member of this group that performed well in the tests described herein. An equally promising result was obtained with perfluorooctanesulfonic acid (3TT), which is not within the scope of '898. This compound would have distinct advantage over 3D in that perfluoroalkylsulfonic acids are known in the art to be much more resistant to chemical and/or thermal degradation than their carboxylic acid counterparts.

There is an additional interesting observation that can be drawn from the results presented in Table 3. The bleed for formulations 3N and 3O, although significantly less than the control, were more than an order of magnitude greater than the measured values for 3B and 3M. Since the cation is identical for all four of these compounds, it is not clear why a difference of anion associated with the quaternary compound should have such a profound effect on bleed. However, it is suspected that it may have something to do with subtle solubility differences. It may be, for example, that both the cyanate and nitrate quaternary ammonium salts have greater affinity for the liquid cyanate monomer phase than either of their bromide or iodide counterparts. This difference in affinity could, in turn, shift the surface-to-liquid equilibrium concentration for the various additives. Presumably, this equilibrium is shifted away from the surface for the nitrate and cyanate salts, and toward the surface for the bromide and iodide salts.

EXAMPLE 5

Screening of potential bleed control agents in filled formulations

The results summarized in Table 3 suggest several classes of compounds that could be used to retard resin bleed in cyanate ester adhesives. Cyanate esters, however, are frequently used in the further presence of fillers. The most useful filler employed for preparation of electrically conductive adhesives is particulate silver. The use of silver, especially silver flake, introduces an additional potential complication into the adhesive system.

It is well known to those of skill in the art that commercially available silver flake is typically coated with one or more lubricants. These lubricants are used because they prevent the silver particles from welding together during the mechanical flaking process. Additionally, the presence of lubricants on the finished flake both promotes rapid dispersion of the silver flake in fluid vehicles and also prevents the agglomeration of flake particles during storage. The most pervasive lubricants used to process silver flake include fatty acids such as oleic and stearic acids. A portion of these lubricants are believed to become bound to the silver surface in the form of silver carboxylate salts. A large excess, however, of these lubricants typically remains on the surface of the silver flake as the free acids. These compounds, as well as their metal salts, are essentially anionic surfactants.

It is well known to those of skill in the art of surface chemistry that anionic and cationic surfactants are incompatable. Specifically, it is well documented that mixtures of these two types of surfactants will result in their mutual precipitation. Non-ionic compounds, such as fatty acid esters of glycerol, sucrose, sorbitol, and the like, would be greatly prefered as silver lubricants since there would not be any risk of incompatability with any of the quaternary bleed retarding agents.

In view of the above considerations, there was a concern that anionic surfactant/cationic surfactant incomparability would occur when silver filler was added to cyanate ester vehicles containing some of the more effective bleed control agents identified in Table 3. A particular silver filler of interest contains a mixture of 68.2% SF84 silver flake (from Degussa - Metz, Corporation), 20.4% EA0095 and 11.4% EA0018 silver flake (both from Chemet Corporation). The principle lubricant on the Degussa-Metz flake is non-ionic, while the lubricant on both of the Chemet flakes is a fatty acid. This silver flake mix was loaded at 80.0% by weight into the 3A, 3B, 3D, 3E, 3I, 3M, 3R, 3S, 3V and 3VV mixtures, as described in Table 3. These paste mixtures were then dotted onto freshly fired gold coupons. The parts were then cured in a 150°±5° C. oven for fifteen minutes. Resin bleed away from the fillet was measured for two test dots from each compostion, as well as the control paste (i.e., 3A) on every one of the test substrates. The results of these tests are presented in Table 4.

TABLE 4

Effect of Additives on Relative Bleed from Silver Filled Cyanate Adhesive

| Designation | | % Bleed Relative to Control |
|---|---|---|
| 3A | None (control) | 100 |
| 3B | Dimethyl dioctadecylammonium bromide | 94 |
| 3D | Perfluorooctanoic acid | 5.0 |
| 3E | Tributyl hexadecylphosphonium bromide | 75 |
| 3I | Hexadecylpyridinium chloride monohydrate | 66 |
| 3M | Dodecyl dimethyloctadecylammonium iodide | 170 |
| 3R | Dodecyl dimethylammonium-3-sulfopropylbetaine | >200 |
| 3S | Dimethyl octadecylammonium-3-sulfopropylbetaine | 92 |
| 3V | N,N-dimethyloctadecylamine | 31 |
| 3VV | N,N,N',N'-tetramethyl-1,20-diamino-(10,11-dioctyl)-eicosane | 15 |

TABLE 5

Combined Effect of Additives and 6% PHS on Relative Bleed

| Designation | | % Bleed Relative to Control |
|---|---|---|
| 3A | None (control) | 100 |
| 3B | Dimethyl dioctadecylammonium bromide | 8.3 |
| 3D | Perfluorooctanoic acid | 7.2 |
| 3E | Tributyl hexadecylphosphonium bromide | 21 |
| 3I | Hexadecylpyridinium chloride monohydrate | 14 |
| 3M | Dodecyl dimethyloctadecylammonium iodide | 3.2 |
| 3R | Dodecyl dimethylammonium-3-sulfopropylbetaine | 170 |
| 3S | Dimethyl octadecylammonium-3-sulfopropylbetaine | 56 |
| 3V | N,N-dimethyloctadecylamine | 16 |
| 3VV | N,N,N',N'-tetramethyl-1,20-diamino-(10,11-dioctyl)-eicosane | 0.0 |

The results presented in Table 4 strongly suggest that significant incompatability exists between the quaternary bleed control agents contemplated for use in the practice of the present invention, and the lubricants employed with silver flake. All of the quaternary bleed control agents had significantly diminished performance in this test, compared to that reported in Table 3. Perfluorooctanoic acid (3D), which is itself an anionic lubricant, was unaffected. The second best performance seen in this test was for the tertiary amines, N,N-dimethyloctadecylamine (3V) and N,N,N',N'-tetramethyl-1,20-diamino-(10,11-dioctyl)-eicosane (3VV). It may be that these compounds retain more of their bleed control efficacy because they are able to neutralize at least a portion of the (excess) stearic acid lubricant, as per the general reaction scheme (Scheme IV):

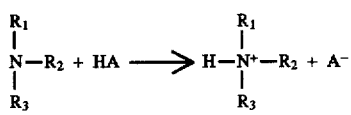

$$\begin{array}{c} R_1 \\ | \\ N-R_2 + HA \longrightarrow H-N^+-R_2 + A^- \\ | \\ R_3 \end{array} \qquad \begin{array}{c} R_1 \\ | \\ \\ | \\ R_3 \end{array} \quad \text{IV}$$

The anti-bleed efficacy of most of the quaternary compounds was either significantly reduced (as in 3B, 3E, 3I, or 3S), relative to results with the unfilled samples (i.e., Example 4), or substantially obliterated (as in 3M and 3R). Presumably, the presence of the free fatty acid lubricants can indeed neutralize some or all of the anti-bleed efficacy of the quaternary onium compounds contemplated for use in the practice of the present invention. It is believed that the incompatibility of the cationic and anionic lubricants results in a decrease in the functional concentration of the quaternary compounds.

EXAMPLE 6

Screening of combinations of potential bleed control agents in filled formulations It appeared that an additional agent was needed to enhance the effectiveness of tertiary amines and/or quaternary onium compounds employed for resin bleed control. The bleed test for the silver pastes was repeated as outlined in Example 5. This time, however, six percent of the vehicle phase (selected from the various vehicle phases referred to in Table 3) was replaced by -325 mesh poly(4-hydroxystyrene). The results from this test are summarized in Table 5.

The addition of powdered poly(4-hydroxystyrene) improved the anti-bleed performance of all of the tertiary amine and/or quaternary compounds tested, indeed, the performance of some of the formulations improved remarkably. The single most impressive result was for the high molecular weight, di-tertiary amine, 3VV. The combination of powdered poly(4-hydroxystyrene) with 3VV resulted in the elimination of any detectable bleed on the parts tested. It is believed that the presence of the polyfunctional compound allows for the most efficient use of the tertiary amine and/or quaternary bleed control agents. Presumably, increasing the rate of cure reduces the opportunity for bleed. The combination of tertiary amine and/or quaternary compounds with polyfunctional curing agents is seen to be much more effective than the use of either additive alone.

EXAMPLE 7

Screening of additional combinations of bleed control agents in filled formulations It was next decided to investigate various polyfunctional cure rate accelerators in the presence and absence of quaternary onium compounds. These materials were tested using a silver filled formulation in order to best simulate a commercial cyanate adhesive system. The base vehicles for this formulation were identical to those summarized in Table 2 (i.e., using the same catalyzed 85:15 mixture of L-10:B-10 base with 5% by weight added polyfunctional compound). The bleed results for pastes made from these vehicles and 80% by weight of the silver flake mix described earlier (see Example 5) are presented in Table 6. None of the quaternary bleed control compounds were added to any of these formulations.

The test pastes were placed onto freshly fired gold plated coupons. Two equal sized drops of these paste compostions were placed on each of the coupons as well as a drop of the control (the cyanate ester vehicle and silver filler without any polyfunctional additives). All of the compostions were cured in an oven at 150±5° C. for fifteen minutes. The solvent bleed from the adhesive fillet was determined at several different points. These values were averaged and then normalized with respect to the control paste.

TABLE 6

Evaluation of Polyfunctional Compounds on Relative Bleed

| Designation | | % Bleed Relative to Control |
|---|---|---|
| 2A | Poly(glycidyl methacrylate) | 79 |
| 2B | Poly(vinyl alcohol) | 180 |
| 2C | Poly(2-hydroxyethyl methacrylate) | 150 |
| 2D | Sucrose monostearate | 51 |
| 2E | Sorbitan monooleate | 38 |
| 2F | 1,1,1-tris(hydroxymethyl)ethane | 94 |
| 2G | Polyglycerol monooleate | 15 |
| 2H | Polyglycerol dioleate | 21 |
| 2I | Poly(4-hydroxystyrene) | 88 |

The bleed of these formulations was lower than the control with the exception of 2B and 2C (poly(vinyl alcohol) and poly(2-hydroxyethyl methacrylate), respectively). The greatest bleed reduction (2G and 2H) was for the mono and dioleoyl esters of polyglycerol.

EXAMPLE 8

Combined effect of polyfunctional compounds and quaternary onium compounds on relative resin bleed Another series of tests were run to further examine the possible synergistic interaction of polyfunctional compounds and quaternary onium compounds. Thus, pastes were formulated from the vehicles described above for Example 2. Silver pastes were made from these vehicles using an 80% loading of the same silver flake mix as described previously. For this experiment, 0.65% of dimethyldioctadecylammonium bromide was also added to each of the test samples. Two controls were used to rate the efficiency of bleed control. The standard control was (as before) the catalyzed cyanate base vehicle mixed into an 80 weight percent silver loaded paste. The additional control run consisted of this same control composition, with the further addition of 0.65% of the above-described quaternary ammonium bromide. All bleed tests were run on clean gold coupons. The bleed results for each test composition were independently normalized to that of both controls. The results from this test are presented in Table 7.

TABLE 7

Combined Effect of Polyfunctional Compounds and Quat on Relative Bleed

| Designation | | % Bleed Relative to Control + Quat | % Bleed Relative to Control |
|---|---|---|---|
| 2A | Poly(glycidyl methacrylate) | 28 | 7.6 |
| 2B | Poly(vinyl alcohol) | 47 | 12 |
| 2C | Poly(2-hydroxyethyl methacrylate) | 102 | 34 |
| 2D | Sucrose monostearate | 31 | 9.1 |
| 2E | Sorbitan monooleate | 48 | 23 |
| 2F | 1,1,1-tris(hydroxymethyl)ethane | 79 | 49 |
| 2G | Polyglycerol monooleate | 52 | 27 |
| 2H | Polyglycerol dioleate | 38 | 17 |
| 2I | Poly(4-hydroxystyrene) | 1.4 | 0.58 |

The results obtained here demonstrate the marked synergism that occurs when both a quaternary bleed control agent and a polyfunctional compound are used together. The best results, in all cases, were obtained when both additives were present. The single most outstanding result was obtained using a combination of dimethyldioctadecylammonium bromide and poly(4-hydroxystyrene).

One additional unanticipated benefit that has been observed with respect to the combined use of quaternary ammonium bleed control agents with the above-described silver flakes and polyfunctional bleed control agents is a significant improvement in the electrical performance of the resulting adhesive. Thus, the average (based on ten parts tested for each group) post cure electrical resistance (through the die) for an untreated control paste was 0.062 ohms at a 1.45 mil bondline. The post cure electrical resistances for the control and 2I pastes at a 2.78 and 2.67 mil bondline were 83.3 and 3.35 ohms, respectively. This dramatic decrease in electrical resistance is considered to be quite advantageous for die attach applications that require electrical conductivity, and is an added unexpected benefit observed for the compositions claimed herein.

While the invention has been described in detail with reference to certain preferred embodiments thereof, it will be understood that modifications and variations are within the spirit and scope of that which is described and claimed.

That which is claimed is:

1. A composition for attaching a device to a substrate, said composition comprising:
   a monomer vehicle comprising at least one polycyanate ester monomer;
   a quantity of a cationic surfactant sufficient to reduce resin bleed upon application of said composition to a substrate; and optionally
   a metal catalyst;
   wherein said composition does not contain a blowing agent.

2. A composition according to claim 1 wherein said monomer vehicle comprises at least two monomers, and wherein at least one monomer is a polycyanate ester monomer.

3. A composition according to claim 1 further comprising a filler.

4. A composition according to claim 3 wherein said filler is thermally and/or electrically conductive.

5. A composition according to claim 1 wherein said cationic surfactant is a quaternary onium compound.

6. A composition according to claim 5 wherein said quaternary onium compound is a quaternary ammonium compound, a quaternary phosphonium compound, or mixtures of any two or more thereof.

7. A composition according to claim 5 wherein said quaternary onium compounds have in the range of about 15 up to about 100 total carbon atoms.

8. A composition according to claim 7 wherein at least one side chain of said quaternary onium compound is at least 12 carbon atoms in length.

9. A composition according to claim 5 wherein said quaternary onium compound is a quaternary ammonium compound.

10. A composition according to claim 9 wherein said quaternary ammonium compound is a distearyldimethylammonium salt, a hexadecylpyridinium salt, a hexadecyldimethylphenylammonium salt, a decyltrimethyl-ammonium salt, a dodecyltrimethylammonium salt, a tetradecyltrimethylammonium salt, a hexadecyltrimethyl-ammonium salt, an octadecyltrimethylammonium salt, an eicosyltrimethylammonium salt, a behenyltrimethylammonium salt, an oleyltrimethylammonium salt, a dioleyldimethylammonium salt, a trioleylmethylammonium salt, a didecyldimethylammonium salt, a didodecyldimethylammonium salt, a ditetradecyldimethylammonium salt, a dihexadecyldimethyl-ammonium salt, a dioctadecyldimethylammonium salt, a dieicosyldimethylammonium salt, a dibehenyldimethylammonium salt, a tridecylmethylammonium salt, a tridodecylmethyl-ammonium salt, a tritetradecylmethylammonium salt, a trihexadecylmethylammonium salt, a trioctadecylmethyl-ammonium salt, a trieicosylmethylammonium salt, a tribehenylmethylammonium salt, oleylhydroxyethyl imidazoline, or mixtures of any two or more thereof.

11. A composition according to claim 5 wherein said quaternary onium compound is a quaternary phosphonium compound.

12. A composition according to claim 11 wherein said quaternary phosphonium compound is selected from a tributylhexadecylphosphonium salt, a hexadecyltriphenyl phosphonium salt, or mixtures of any two or more thereof.

13. A composition according to claim 9 further comprising a polyfunctional compound.

14. A composition according to claim 13 wherein said polyfunctional compound is poly(4-hydroxystyrene).

15. A composition for attaching a device to a substrate, said composition comprising:

monomer vehicle comprising at least one polycyanate ester monomer;

filler; and a quantity of a cationic surfactant sufficient to reduce resin bleed upon application of said composition to a substrate;

wherein said composition does not contain a blowing agent.

16. A composition according to claim 15 wherein said monomer vehicle is present in an amount falling in the range of about 8 to 80 weight percent, based on the total weight of the composition.

17. A composition according to claim 15 wherein said filler is thermally and/or electrically conductive.

18. A composition according to claim 17 wherein said filler is present in an amount falling in the range of about 20 to 92 weight percent, based on the total weight of the composition.

19. A composition according to claim 15 further comprising 50 to 1500 ppm metal catalyst.

20. A composition according to claim 15 wherein said cationic surfactant is a quaternary onium compound.

21. A composition according to claim 20 wherein said quaternary onium compound is a quaternary ammonium compound, a quaternary phosphonium compound, or mixtures of any two or more thereof.

22. A composition according to claim 20 wherein said quaternary onium compounds have in the range of about 15 up to about 100 total carbon atoms.

23. A composition according to claim 22 wherein at least one side chain of said quaternary onium compound is at least 12 carbon atoms in length.

24. A composition according to claim 20 wherein said quaternary onium compound is a quaternary ammonium compound.

25. A composition according to claim 24 wherein said quaternary ammonium compound is a distearyldimethylammonium salt, a hexadecylpyridinium salt, a hexadecyldimethylphenylammonium salt, a decyltrimethyl-ammonium salt, a dodecyltrimethylammonium salt, a tetradecyltrimethylammonium salt, a hexadecyltrimethyl-ammonium salt, an octadecyltrimethylammonium salt, an eicosyltrimethylammonium salt, a behenyltrimethylammonium salt, an oleyltrimethylammonium salt, a dioleyldimethylammonium salt, a trioleylmethylammonium salt, a didecyldimethylammonium salt, a didodecyldimethylammonium salt, a ditetradecyldimethylammonium salt, a dihexadecyldimethyl-ammonium salt, a dioctadecyldimethylammonium salt, a dieicosyldimethylammonium salt, a dibehenyldimethylammonium salt, a tridecylmethylammonium salt, a tridodecylmethyl-ammonium salt, a tritetradecylmethylammonium salt, a trihexadecylmethylammonium salt, a trioctadecylmethyl-ammonium salt, a trieicosylmethylammonium salt, a tribehenylmethylammonium salt, oleylhydroxyethyl imidazoline, or mixtures of any two or more thereof.

26. A composition according to claim 20 wherein said quaternary onium compound is a quaternary phosphonium compound.

27. A composition according to claim 26 wherein said quaternary phosphonium compound is selected from a tributylhexadecylphosphonium salt, a hexadecyltriphenyl phosphonium salt, or mixtures of any two or more thereof.

28. A composition according to claim 20 further comprising a polyfunctional compound.

29. A composition according to claim 28 wherein said polyfunctional compound is poly(4-hydroxystyrene).

30. A method for reducing resin bleed of cyanate ester-containing compositions upon application to a substrate, said method comprising adding to said composition a quantity of a cationic surfactant sufficient to reduce resin bleed upon application of said composition to a substrate, wherein said composition does not contain a blowing agent.

31. A method according to claim 30 wherein the quantity of bleed control agent falls in the range of about 0.1 up to about 10 weight percent of the organic fraction of said cyanate ester-containing composition.

32. A method according to claim 30 wherein said cationic surfactant is a quaternary onium compound.

33. A method according to claim 32 wherein the quantity of cationic surfactant falls in the range of about 0.1 up to 3 weight percent of the organic fraction of said cyanate ester-containing composition.

* * * * *